(12) United States Patent
Lessure et al.

(10) Patent No.: US 7,592,595 B1
(45) Date of Patent: Sep. 22, 2009

(54) WIDE CONCENTRATION RANGE GAS DETECTION

(75) Inventors: Harold S. Lessure, Pittsburgh, PA (US); Satoru Simizu, Pittsburgh, PA (US); Kirankumar M. Kothari, Hoffman Estates, IL (US)

(73) Assignee: Operations Technology Development, NFP, Des Plaines, IL (US)

( * ) Notice: Subject to any disclaimer, the term of this patent is extended or adjusted under 35 U.S.C. 154(b) by 20 days.

(21) Appl. No.: 11/545,004

(22) Filed: Oct. 6, 2006

Related U.S. Application Data (60) Provisional application No. 60/786,499, filed on Mar. 28, 2006.

(51) Int. Cl.
*G01J 5/58* (2006.01)

(52) U.S. Cl. .................................. 250/339.01

(58) Field of Classification Search .............. 250/343, 250/339.01, 339.02, 339.03, 339.04, 339.05, 250/339.06, 339.07, 339.08, 339.09, 339.1, 250/339.11, 339.12, 339.13, 339.14, 339.15, 250/344, 345, 346
See application file for complete search history.

(56) References Cited

U.S. PATENT DOCUMENTS 4,958,076 A * 9/1990 Bonne et al. ................ 250/343
5,438,406 A * 8/1995 Puschell ..................... 356/307
5,886,348 A * 3/1999 Lessure et al. .......... 250/339.13
6,107,925 A * 8/2000 Wong ........................ 340/628
6,469,303 B1 * 10/2002 Sun et al. .................... 250/343
7,004,909 B1 * 2/2006 Patel et al. .................. 600/532
7,397,568 B2 * 7/2008 Bryce et al. ................. 356/484
2004/0000643 A1 * 1/2004 Karlsson ................ 250/339.13
2006/0098202 A1 * 5/2006 Willing et al. .............. 356/437
2007/0246653 A1 * 10/2007 Zhou ....................... 250/339.1

* cited by examiner

*Primary Examiner*—David P Porta
*Assistant Examiner*—David S Baker
(74) *Attorney, Agent, or Firm*—Mark E. Fejer (57) ABSTRACT

A method and apparatus in which a first absorption measurement is made over a first frequency interval or set of frequency intervals including one or more absorptions from a spectral band of interest. The first absorption measurement is ideally selected to be near the frequency of a peak in the absorption spectrum, providing high sensitivity at low gas concentrations. A second absorption measurement is made over a second frequency interval. The second absorption measurement is made to include a contribution from the broadening of the absorption spectrum at higher concentrations. The second absorption measurement provides sensitivity at higher concentrations. The two absorption measurements are then combined to deduce the target sample concentration as the absorption line spectrum changes shape with concentration.

13 Claims, 7 Drawing Sheets

WIDE CONCENTRATION RANGE GAS DETECTION

CROSS REFERENCE TO RELATED APPLICATION

This application claims the benefit of Provisional U.S. Patent Application Ser. No. 60/786,499 filed 28 Mar. 2006.

BACKGROUND OF THE INVENTION

This invention relates to a method and apparatus for sensitive high speed spectroscopic gas detection over a wide range of gas concentrations from less than one (1) part per million (ppm) up to 100%.

In general, the transmission or absorption of radiation passing through a radiation absorbing medium, such as a gas, may be graphed as a function of wavelength or frequency as an optical absorption spectrum. The absorption spectrum consists of a set of discrete absorption lines characteristic of the gas of interest. In general, absorption measurements within a narrow frequency interval and comparable or smaller than the line width near an absorption peak can be used as a sensitive measure of the number or concentration of absorbing gas molecules present. At very large concentrations, all of the radiation within a small frequency interval near an absorption peak is heavily absorbed. This is called absorption line saturation. However, when measurements are made away from the peak absorption frequency or over a wider spectrum where the frequency interval of measurement is larger, the absorption measurement includes contributions from frequencies which are not saturated. These off-line absorption measurements are highly dependent on the shape of the absorption lines. Line shape dependent measurements include the integrated absorption over an entire line or multiple absorption lines grouped into bands which are characteristic of the absorbing species.

A typical method of measuring gas concentration relies upon absorption of electromagnetic radiation by the target gas atoms or molecules when electromagnetic radiation is passed through a sample containing a gas which absorbs some of the radiation. However, such known methods are limited with respect to the range of concentrations over which the target gas atoms or molecules can be detected.

SUMMARY OF THE INVENTION

Accordingly, it is one object of this invention to provide a method for measuring the concentration of a gas from very low concentrations to very high concentrations, that is, from less than 1 part-per-million (ppm) up to 100% gas.

This object is addressed by a method in which a first absorption measurement is made over a first frequency interval or set of frequency intervals in which is one or more absorptions from a spectral band of interest. The first absorption measurement is ideally selected to be near the frequency of a peak in the absorption spectrum. This provides high sensitivity at low gas concentrations. A second absorption measurement is made over a second frequency interval or set of frequency intervals. The second absorption measurement is made to include a contribution from the broadening of the absorption spectrum at higher concentrations. The second absorption measurement provides sensitivity at higher concentrations. The two absorption measurements are then combined to deduce the target sample concentration as the absorption line spectrum changes shape with concentration.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

Figure 1:
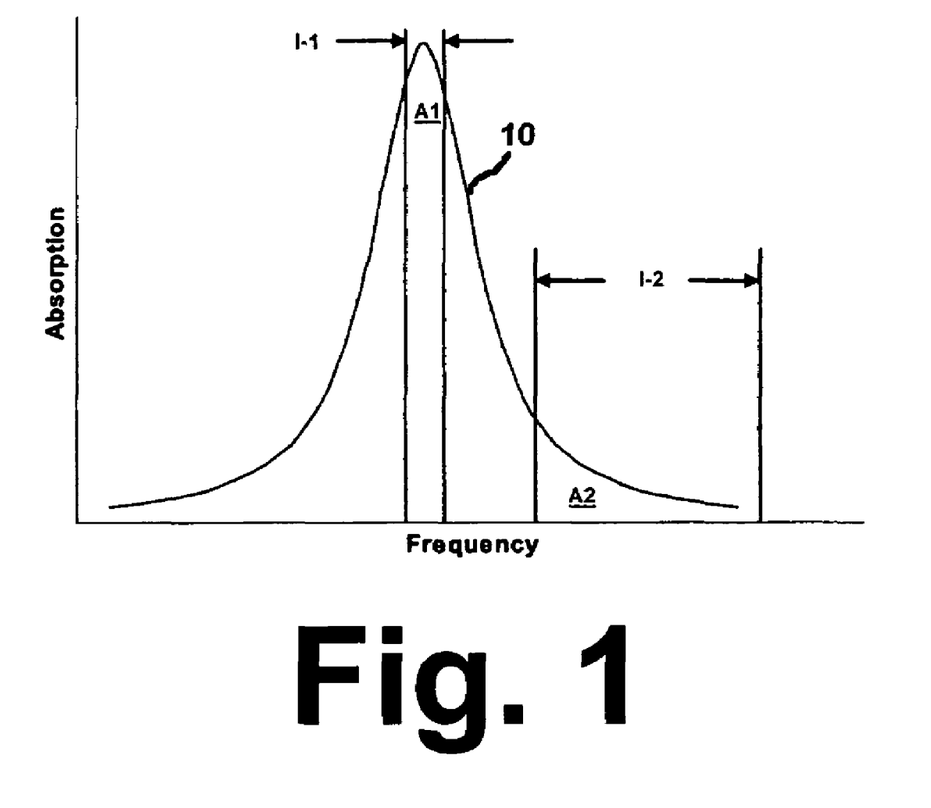
FIG. 1 is a diagram showing absorption measurements made over two frequency intervals for a single Lorentz absorption line in accordance with one embodiment of this invention.

The invention claimed herein is a method for measuring the concentration of a gas in which a measurement of a first electromagnetic absorption (A1) by the gas over a first frequency interval (I-1) is combined with a measurement of a second electromagnetic radiation absorption (A2) over a second frequency interval (I-2). FIG. 1 shows a diagram of exemplary absorptions and frequency intervals. The first measurement A1 is made over a wavelength interval I-1, which is a subsection of the absorption line 10. The second measurement A2 shown in FIG. 1 is made over a second measurement interval I-2. In general, the intervals I-1 and I-2 may be any convenient interval for the measurement. The intervals may overlap and may include multiple absorption lines although the measurement intervals in FIG. 1 are shown as distinct intervals over a single absorption line for the sake of clarity.

Figure 2:
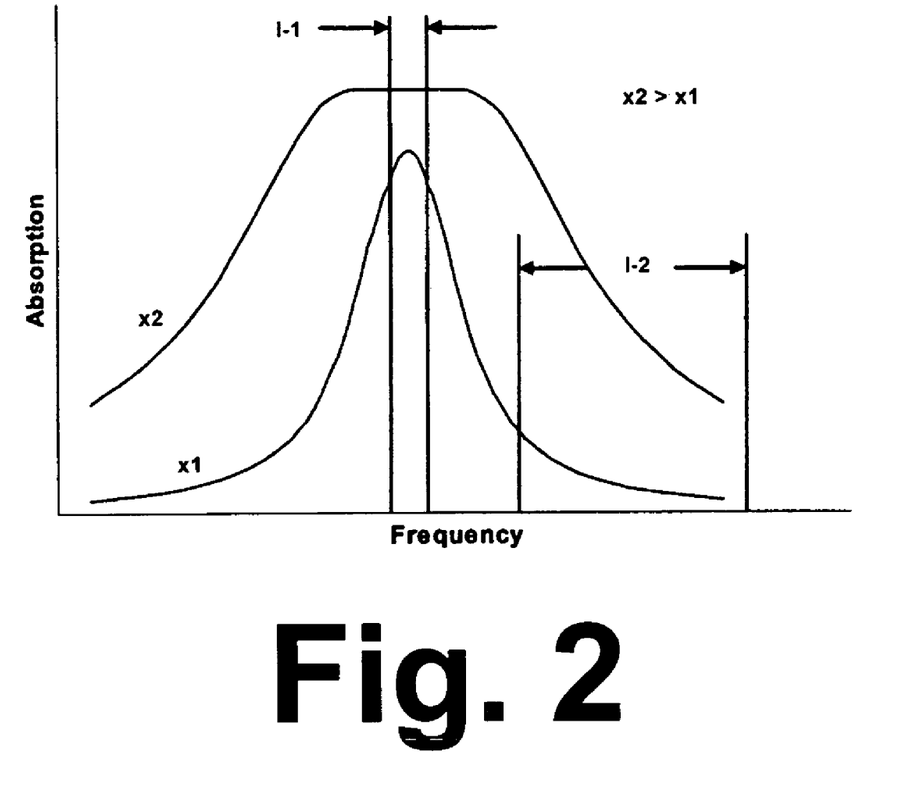
FIG. 2 is a diagram showing the effect of line saturation and broadening on the absorption line for two concentrations, ×1 and ×2, in which ×2 is greater than ×1.

As previously indicated, off-line absorption measurements are highly dependent on the shape of the absorption lines. Line shape dependent measurements include the integrated absorption over an entire line or multiple absorption lines grouped into bands which are characteristic of the absorbing species. FIG. 1 shows a narrow band absorption section near the peak and another absorption section away from the peak on a single absorption line having a Lorentz line shape. Those skilled in the art will appreciate that this description is readily extended to multiple lines or different line shapes. Clearly the two absorption measurements are affected by the shape of the line or lines within the frequency measurement interval. At low concentrations, sensitive measurements may be obtained by measuring changes in absorption at or near the peak absorption frequency. These peak absorption measurements quantify the magnitude or height of the absorption line. The net absorption within the frequency interval is represented by the areas A1 and A2 under the curve in FIG. 1. At higher concentrations, the absorption line saturates and the principle change in absorption comes from broadening of the width of the line. This saturation effect is shown in FIG. 2.

The detailed variation of shape of absorption lines with concentration is influenced by a number of factors. The principal physical cause of line broadening is collisions between gas atoms or molecules. These collisions are affected primarily by the temperature and pressure or concentration of the gas. A key feature of the line shape is the variation of line width with pressure or concentration. This line broadening is sometimes called collisional broadening, pressure broadening or Lorentz broadening of the line.

Figure 3:
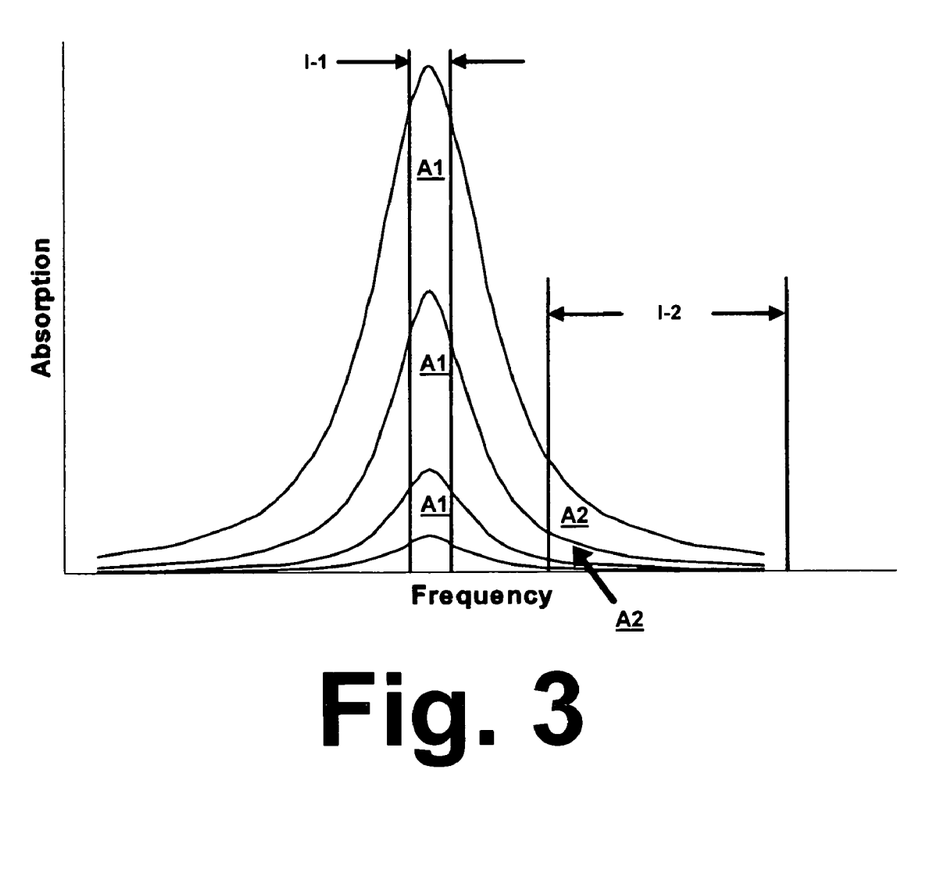
FIG. 3 is a diagram showing the progressive increases associated with increases in concentration in the absorption of a frequency interval at low concentrations.
Figure 4:
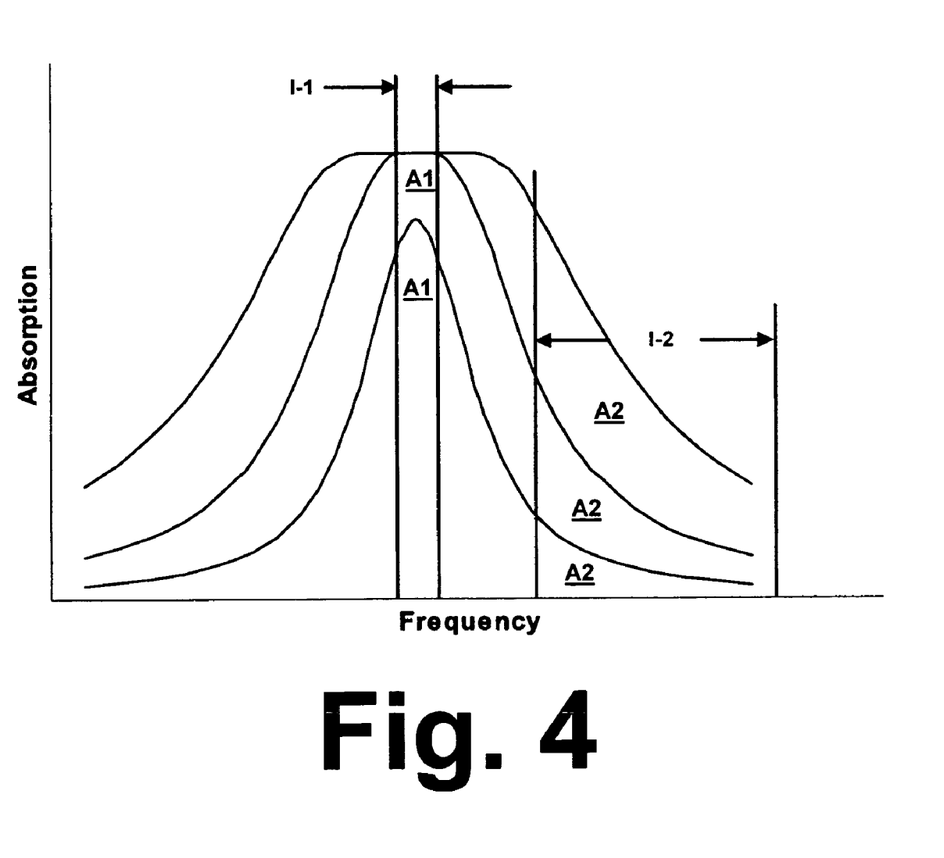
FIG. 4 is a diagram showing the saturation of absorption over the interval of FIG. 3 and progressive absorption due to line broadening within a second interval at higher gas concentrations.

The effect of line broadening on an absorption measurement can be discussed using diagrams. At low concentrations, the situation is shown in FIG. 3 for progressively higher concentrations of gas. The two absorption measurements are shown over frequency intervals I-1 and I-2. The associated absorptions A1 and A2 are represented by the areas under the curves in these two intervals. The interval I-1 is set at or near the absorption peak. The second interval I-2 is away from the peak. FIG. 3 shows how the absorption measurement A1 at low concentrations varies with the changing magnitude (height of the line). FIG. 4 shows the situation at high concentrations where the line is saturated in the interval I-1 but the absorption A2 increases due to line broadening.

Here we discuss the broadening of a Lorentz line shape, but those skilled in the art will appreciate that the method applies to any line shape which varies with concentration of the absorbing species. The pressure variation of linewidth is well known for a Lorentz line shape and is given by $$\Delta v = (\Delta v)_0 \frac{P}{P_0} \left(\frac{T}{T_0}\right)^{-\frac{1}{2}}$$

and may be more generally represented as a power law in both normalized pressure and temperature for other line shapes:

$$\Delta v = (\Delta v)_0 \left(\frac{P}{P_0}\right)^m \left(\frac{T}{T_0}\right)^n$$

where $(\Delta v)_0$ is the linewidth at the standard pressure $P_0$ and temperature $T_0$, P is the effective pressure reflecting the partial pressure or concentration of the gas, T the temperature, and m and n are the pressure broadening and temperature broadening exponents, respectively. At constant temperature or near the standard temperature, the temperature effect is either constant or negligible. At low concentrations where the effective pressure is near the standard pressure, the ratio of $P/P_0$ is nearly 1 and the pressure induced broadening also can be neglected. At high concentrations corresponding to high partial pressures of the target gas, a major contribution to the absorption comes about due to the increase in the line width.

There are several ways in which the two frequency intervals I-1 and I-2 may be selected and absorption measurements A1 and A2 may be made. These include, but are not limited to 1) I-1 and I-2 selected with fixed bandpass filters; 2) I-1 selected with a tunable filter and I-2 selected with a fixed bandpass filter; 3) I-1 selected with a fixed bandpass filter and I-2 selected with a tunable filter; 4) I-1 and I-2 selected with a tunable filter; 5) I-1 selected by a tunable filter and I-2 selected by the light source spectrum such as with a laser or LED; and 6) I-1 selected by a fixed bandpass filter and I-2 selected by the light source spectrum such as with a laser or LED.

It is to be understood that I-1 and I-2 may be distinct non-overlapping frequency or wavelength intervals or, alternatively, the intervals I-1 and I-2 may partially or completely overlap. Also, it is to be understood that there are many ways to select the intervals I-1 and I-2 other than the few listed above.

Figure 5:
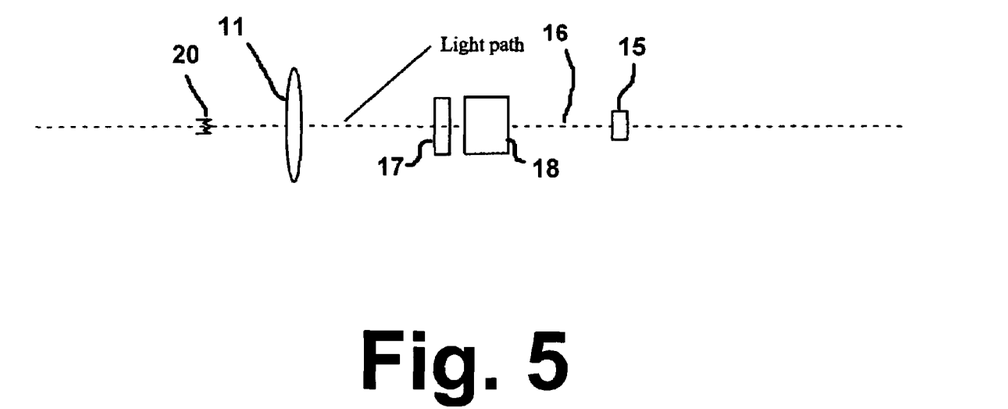
FIG. 5 is a diagram showing a single optical element line broadening gas detector for use in the method of this invention.
Figure 6:
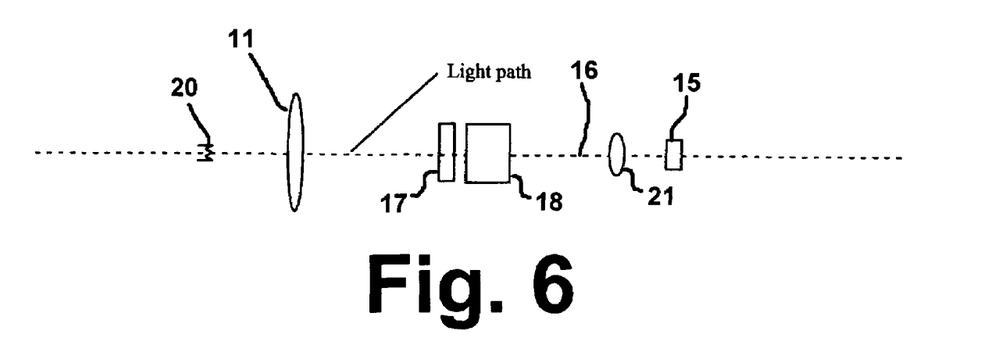
FIG. 6 is a diagram showing a two optical element line broadening gas detector for use in the method of this invention.

The preferred technique for making the measurement is where I-1 is selected by a tunable filter and I-2 is selected by a fixed bandpass filter. FIG. 5 and FIG. 6 show schematic diagrams of specific implementations of the technique. Both implementations comprise a source (S) of electromagnetic radiation, i.e. light, 20 and an optical element 11 to direct the light towards a detector 15. Optical element 11 may be either a transmitting element such as a lens or a reflecting element such as a mirror. The light path is defined schematically by the dashed lines 16 and the absorbing species to be detected would be present in the light path. Both implementations further comprise a first filter 17 to define the wavelength interval I-2 for the second absorption measurement and a second filter 18 which is used to make a measurement over a wavelength subinterval I-1. Filter 18 in accordance with one embodiment of this invention is an electro-optical modulator (EOM) where the interval I-1 is defined by the electrical tuning range of the EOM. A simple example of an appropriate EOM is a transverse electro-optic modulator. Electro-optic modulators are described extensively in standard textbooks. The radiation is then incident on a detector 15 as in FIG. 5 or the radiation is directed using a second optical element 21 onto the detector 15 as shown in FIG. 6. FIG. 6 is similar to the gas detector shown in FIG. 5 with the addition of the second optical element 21 which may again be a transmitting or reflecting element to assist in directing the light signal onto the detector 15. The detector may be any type appropriate for the radiation to be detected. One example of a candidate detector is a photodiode. The detection instrument includes electronics to control the temperature of the instrument, tune the transmission of EOM, and produce signals from the detector which represent the absorptions due to any absorbing species present in the light path. Although this technique describes the use of an electro-optic modulator, other types of optical tunable filters could be used including acousto-optic tunable filters, spacing or angle tuned etalons, or other means for obtaining a tunable filter response over the interval of interest.

Figure 7:
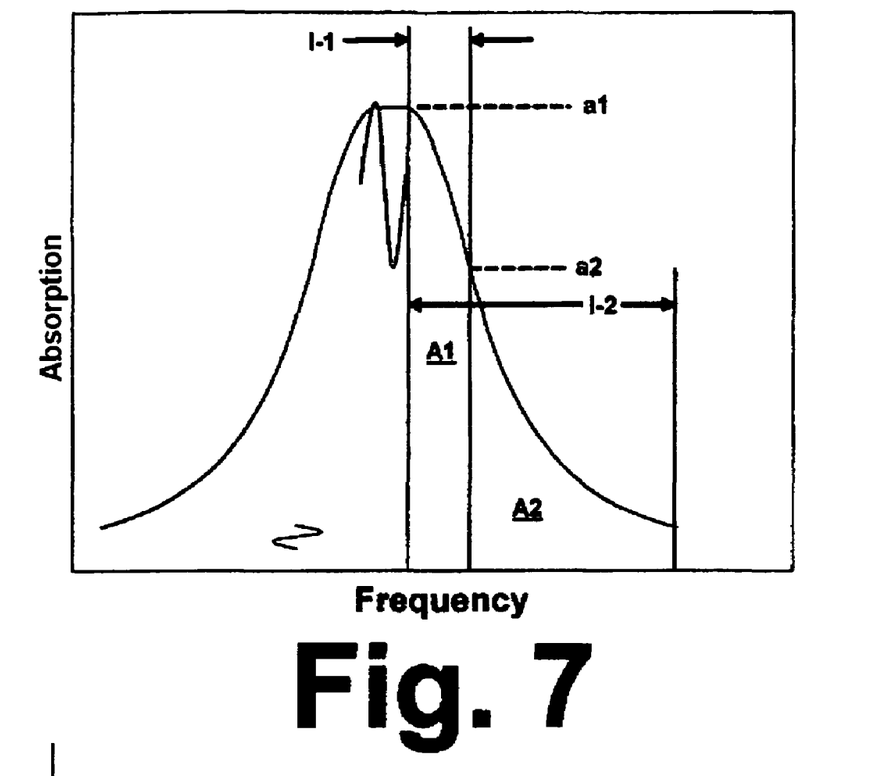
FIG. 7 is a diagram showing a representation of absorption signals for wide dynamic range gas concentration measurement in accordance with the method of this invention.
Figure 8:
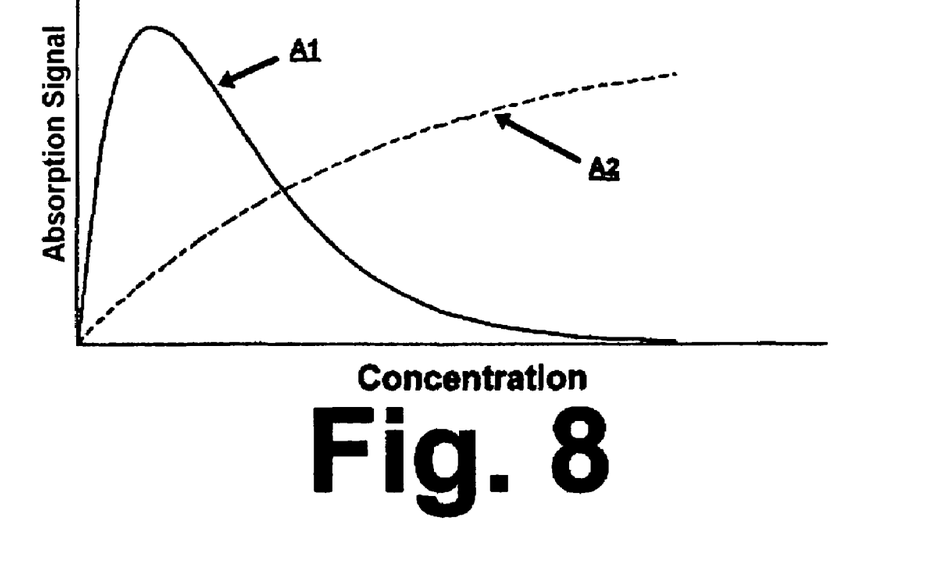
FIG. 8 is a diagram showing representative absorption signals over the two frequency intervals employed in the method of this invention.
Figure 9:
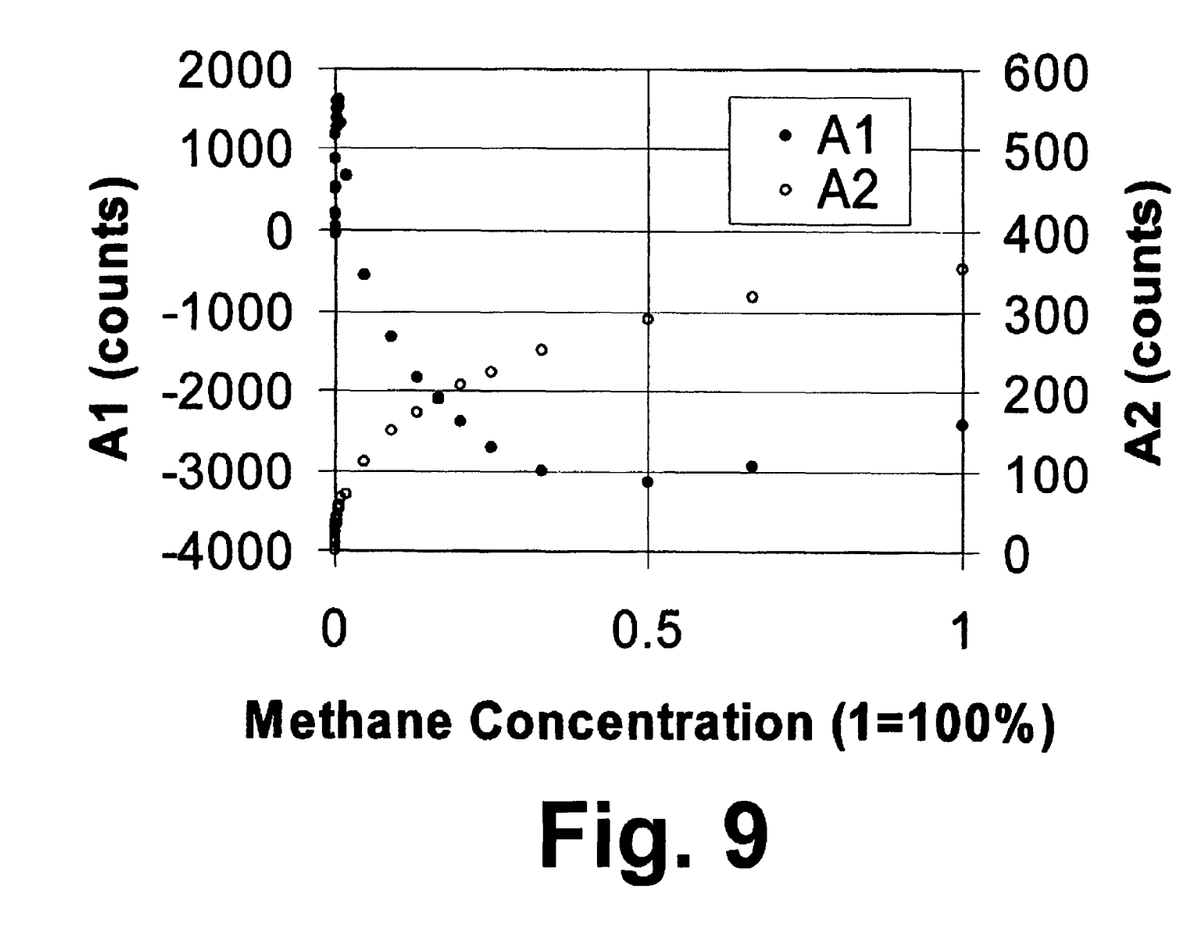
FIG. 9 is a diagram showing data obtained from application of the method of this invention to a methane gas sample.

The absorption signals produced by this arrangement are illustrated in FIG. 7. The filter 18 is modulated electronically to produce a time varying signal as the filter transmission is modulated over the interval I-1. The tunable filter is modulated over I-1 between absorption values a1 and a2 as shown in FIG. 7. The signal amplitude A1 which serves as a measure of the absorption over interval I-1 is proportional to the change in absorption values a1 and a2, A1=b*(a1−a2) where b is a proportionality constant for modulations which are small relative to the line width. The absorption signal A1 is a measure of the absorption change or derivative of the line over the interval I-1. A2 is the area under the curve over interval I-2. The filter 17 selects a measurement window I-2 and the absorption A2 is represented by the area under the curve defined by the combined filtering effect of both filters 17 and 18. The sample concentration is derived as a function of the two absorption signals C=f(A1, A2). The signals A1 and A2 are plotted schematically in FIG. 8 as a function of gas concentration from zero concentration to 100% gas for a fixed measurement path length. The signal A1 is seen to rise linearly at low concentrations, peak when the slope of the line is highest, and then decrease as the concentration becomes large enough to produce absorption line saturation and the linewidth broadens further. Since the absorption signal A1 is not monotonic with concentration, there is an ambiguity in determining the concentration from the signal A1 alone. The absorption A2 may be explained using Beer's law for the change in transmission intensity I of the radiation:

$$I(v)=I_0(v)e^{-ax}$$

where
  a=k(v)L
  k=gas absorption coefficient
  L=optical pathlength
  x=gas concentration
  v=frequency The transmission is expressed as T=I/Io which falls exponentially with increasing concentration (x) and the absorption is A=1−T. Note that the absorption coefficients are frequency or wavelength dependent and, thus, the appropriate absorption may be selected by choosing the measurement frequency or wavelength interval carefully and summing or integrating the response over the measurement interval. The signal A2 from interval I-2 also rises linearly, but it is monotonic and does not saturate at the higher concentrations so that the additional measurement of A2 removes the ambiguity. There is only one concentration which produces a given pair of absorption signals A1 and A2. FIG. 9 shows the results obtained from application of the method of this invention to a methane gas sample.

Although the discussion above relates to a single absorption line, the argument may be used for multiple absorption lines each having an associated absorption A1, over a first measurement interval I-1, and second absorption A2, measurement interval I-2, and summing the absorptions of the intervals.

$$A1 = \sum_n A1_n$$

$$A2 = \sum_n A2_n$$

It is also to be understood that a filter having a periodic filter response may optionally be designed to match a set of absorption lines of a target absorbing species if desired and the contributions from a set of lines be summed using this technique.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for measuring gas concentrations comprising the steps of:
   determining a spectral band having at least one absorption frequency for a gas of interest;
   measuring a first positive absorption by said gas over at least one first frequency interval within said spectral band;
   measuring a second positive absorption by said gas over at least one second frequency interval within said spectral band, said at least one second frequency interval having at least one different line broadened absorption than said at least one first frequency interval; and
   determining said gas concentration from a combination of said measurements over said at least one first frequency interval and said at least one second frequency interval.

2. A method in accordance with claim 1, wherein said first positive absorption measurement is made proximate a frequency of a peak in said spectral band.

3. A method in accordance with claim 1, wherein said first frequency interval is selected by one of a fixed bandpass filter, a tunable filter, and a light source spectrum.

4. A method in accordance with claim 3, wherein said second frequency interval is selected by one of said fixed bandpass filter, said tunable filter, and said light source spectrum.

5. A method in accordance with claim 1, wherein said gas concentration is in a range of about 1 part per million (ppm) to 100%.

6. A method for measuring gas concentrations comprising the steps of:
   determining a spectral band having at least one absorption frequency for a gas of interest;
   measuring a first positive absorption by said gas over a first frequency interval within said spectral band, said first positive absorption associated with one of gas concentration variations at lower gas concentrations and gas concentration variations at higher gas concentrations, said lower gas concentrations having a lower limit value of about 1 ppm and an upper limit value of less than 100% and said higher gas concentrations having a lower limit value greater than 1 ppm and an upper limit value of 100%;
   measuring a second positive absorption by said gas over a second frequency interval within said spectral band, said second positive absorption associated with the other of said gas concentration variations at lower gas concentrations and said gas concentration variations at higher gas concentrations;
   determining a first absorption change in said first positive absorption over said first frequency interval, said first absorption change correlating with a first change in concentration of said gas;
   determining a second absorption change in said second positive absorption over said second frequency interval, said second absorption change correlating with a second change in concentration of said gas; and
   determining a gas concentration of said gas from a combination of said first change in concentration of said gas and said second change in concentration of said gas.

7. A method in accordance with claim 6, wherein said lower gas concentration corresponds to a frequency of a peak in said spectral band.

8. A method in accordance with claim 6, wherein said first frequency interval encompasses a frequency peak in said spectral band.

9. A method in accordance with claim 6, wherein said frequency intervals are selected by a frequency interval selector selected from the group consisting of a fixed bandpass filter, a tunable filter, a light source spectrum and combinations thereof.

10. A system for measuring transmission or absorption of electromagnetic radiation by an electromagnetic radiation absorbing gas comprising:
- a light source;
- a light detector;
- a light path extending from said light source to said light detector;
- an optical element directing light from said light source to said light detector;
- first wavelength means for defining a first wavelength interval;
- second wavelength means for defining a second wavelength interval;
- a light absorbing species of interest disposed in said light path; and
- a data analyzer measuring a first positive absorption by said light absorbing species of interest over said first wavelength interval, measuring a second positive absorption by said light absorbing species of interest over said second wavelength interval, calculating a first absorption change in said first positive absorption over said first wavelength interval, calculating a second absorption change in said second positive absorption over said second wavelength interval, and determining a concentration of said electromagnetic radiation absorbing gas from a combination of said first absorption change and said second absorption change.

11. A system in accordance with claim 10, wherein said first wavelength means comprises one of a fixed bandpass filter, a tunable filter, and a light source spectrum.

12. A system in accordance with claim 10, wherein said second wavelength means comprises one of a fixed bandpass filter, a tunable filter, and a light source spectrum.

13. A method for measuring concentrations of a gas of interest in a gas sample comprising said gas of interest, the method comprising the steps of:
- determining a spectral band having at least one absorption frequency for said gas of interest;
- measuring a first positive absorption by said gas of interest in said gas sample over at least one first frequency interval within said spectral band;
- measuring a second positive absorption by said gas of interest in said gas sample over at least one second frequency interval within said spectral band, said at least one second frequency interval having at least one different line broadened absorption than said at least one first frequency interval; and
- determining said concentration of said gas of interest in said gas sample from a combination of said measurements over said at least one first frequency interval and said at least one second frequency interval.

* * * * *